(12) United States Patent  
Palti

(10) Patent No.: US 8,170,684 B2  
(45) Date of Patent: May 1, 2012

(54) ELECTRODES FOR APPLYING AN ELECTRIC FIELD IN-VIVO OVER AN EXTENDED PERIOD OF TIME

(75) Inventor: Yoram Palti, Haifa (IL)

(73) Assignee: Novocure Limited, St. Helier (JE)

( * ) Notice: Subject to any disclaimer, the term of this patent is extended or adjusted under 35 U.S.C. 154(b) by 296 days.

(21) Appl. No.: 12/729,545

(22) Filed: Mar. 23, 2010

(65) Prior Publication Data

US 2010/0179621 A1 Jul. 15, 2010

Related U.S. Application Data

(62) Division of application No. 11/294,780, filed on Dec. 5, 2005, now Pat. No. 7,715,921.

(60) Provisional application No. 60/633,871, filed on Dec. 7, 2004.

(51) Int. Cl.  
*A61N 1/40* (2006.01)

(52) U.S. Cl. ............ 607/76; 600/15; 607/115; 607/152; 607/154

(58) Field of Classification Search .................. None  
See application file for complete search history.

(56) References Cited

U.S. PATENT DOCUMENTS

| | | | |
|---|---|---|---|
| 2,220,269 A | 11/1940 | Patzold et al. | |
| 3,915,151 A * | 10/1975 | Kraus | 600/13 |
| 3,991,770 A | 11/1976 | LeVeen | |
| 4,016,886 A | 4/1977 | Doss et al. | |
| 4,121,592 A | 10/1978 | Whalley | |
| 4,140,130 A * | 2/1979 | Storm, III | 607/154 |
| 4,263,920 A | 4/1981 | Tasto et al. | |
| 4,367,755 A * | 1/1983 | Bailey | 607/152 |
| 4,467,809 A | 8/1984 | Brighton | |
| 4,472,506 A | 9/1984 | Liburdy | |
| 4,622,952 A | 11/1986 | Gordon | |
| 4,626,506 A | 12/1986 | Arnold et al. | |
| 4,676,258 A | 6/1987 | Inokuchi et al. | |
| 4,822,470 A | 4/1989 | Chang | |
| 4,846,178 A | 7/1989 | Fuxue et al. | |
| 4,846,196 A | 7/1989 | Wiksell et al. | |

(Continued)

FOREIGN PATENT DOCUMENTS

EP 0330797 9/1989

(Continued)

OTHER PUBLICATIONS

Hofmann et al., "Electronic Genetic-Physical and Biological Aspects of Cellular Electomanipulation", IEEE Eng. in Med. and Biology Mag., Dec. 1986, p. 6-23, New York.

(Continued)

*Primary Examiner* — Kennedy Schaetzle  
(74) *Attorney, Agent, or Firm* — Proskauer

(57) ABSTRACT

As compared to conventional electrodes, the electrode configurations disclosed herein minimize irritation and damage to the skin when they are placed in contact with a patient's body over extended of time. The electrodes are formed from a conductive substrate coated with a thin dielectric material, and a plurality of open spaces pass through the electrodes. Those open spaces are distributed and sized to permit moisture on the surface of the patient's body to escape when the electrode is placed in contact with the patient's body. One intended use for the electrodes is for treating tumors by applying an AC electric field with specific frequency and field strength characteristics over an extended period of time.

27 Claims, 6 Drawing Sheets

U.S. PATENT DOCUMENTS

| | | | |
|---|---|---|---|
| 4,923,814 | A | 5/1990 | Marshall |
| 4,936,303 | A | 6/1990 | Derwiler et al. |
| 4,971,991 | A | 11/1990 | Umemura et al. |
| 5,099,756 | A | 3/1992 | Franconi et al. |
| 5,158,071 | A | 10/1992 | Umemura et al. |
| 5,236,410 | A | 8/1993 | Granov et al. |
| 5,269,304 | A | 12/1993 | Matthews |
| 5,312,813 | A | 5/1994 | Costerton et al. |
| 5,386,837 | A | 2/1995 | Sterzer |
| 5,389,069 | A | 2/1995 | Weaver |
| 5,441,532 | A | 8/1995 | Fenn |
| 5,441,746 | A | 8/1995 | Chagnon |
| 5,468,223 | A | 11/1995 | Mir |
| 5,606,971 | A | 3/1997 | Sarvazyn |
| 5,674,267 | A | 10/1997 | Mir et al. |
| 5,718,246 | A | 2/1998 | Vona |
| 5,807,257 | A | 9/1998 | Bridges |
| 5,964,726 | A | 10/1999 | Korenstein et al. |
| 5,976,092 | A | 11/1999 | Chinn |
| 5,984,882 | A | 11/1999 | Rosenchein et al. |
| 6,027,488 | A | 2/2000 | Hofmann et al. |
| 6,043,066 | A | 3/2000 | Mangano et al. |
| 6,055,453 | A | 4/2000 | Hofmann et al. |
| 6,068,650 | A | 5/2000 | Hofmann et al. |
| 6,096,020 | A | 8/2000 | Hofmann et al. |
| 6,319,901 | B1 | 11/2001 | Bernard et al. |
| 6,366,808 | B1 | 4/2002 | Schroeppel et al. |
| 6,413,255 | B1 | 7/2002 | Stern |
| 6,447,499 | B2 | 9/2002 | Gray |
| 6,856,839 | B2 | 2/2005 | Litovitz |
| 6,868,289 | B2 | 3/2005 | Palti |
| 7,016,725 | B2 | 3/2006 | Palti |
| 7,089,054 | B2 | 8/2006 | Palti |
| 7,136,699 | B2 | 11/2006 | Palti |
| 7,146,210 | B2 | 12/2006 | Palti |
| 7,333,852 | B2 | 2/2008 | Palti |
| 7,467,011 | B2 | 12/2008 | Palti |
| 7,519,420 | B2 | 4/2009 | Palti |
| 7,565,205 | B2 | 7/2009 | Palti |
| 7,565,206 | B2 | 7/2009 | Palti |
| 2002/0193832 | A1 | 12/2002 | Gray |
| 2002/0193833 | A1 | 12/2002 | Dimmer et al. |
| 2003/0060856 | A1 | 3/2003 | Chornenky et al. |
| 2003/0191506 | A1 | 10/2003 | Shloznilov |
| 2004/0068296 | A1 | 4/2004 | Palti |
| 2005/0209640 | A1 | 9/2005 | Palti |
| 2005/0209641 | A1 | 9/2005 | Palti |
| 2005/0240173 | A1 | 10/2005 | Palti |
| 2005/0240228 | A1 | 10/2005 | Palti |
| 2006/0149341 | A1 | 7/2006 | Palti |
| 2006/0233867 | A1 | 10/2006 | Palti |
| 2006/0241547 | A1 | 10/2006 | Palti |
| 2006/0276858 | A1 | 12/2006 | Palti |
| 2006/0282122 | A1 | 12/2006 | Palti |
| 2007/0033660 | A1 | 2/2007 | Palti |
| 2007/0184020 | A1 | 8/2007 | Kalbe et al. |
| 2007/0225766 | A1 | 9/2007 | Palti |
| 2007/0239213 | A1 | 10/2007 | Palti |
| 2008/0221630 | A1 | 9/2008 | Palti |
| 2008/0319372 | A1 | 12/2008 | Palti |
| 2009/0043346 | A1 | 2/2009 | Palti |
| 2009/0076366 | A1 | 3/2009 | Palti |

FOREIGN PATENT DOCUMENTS

| | | |
|---|---|---|
| GB | 1419660 | 12/1975 |
| GB | 2026322 | 2/1980 |
| GB | 2043453 | 10/1980 |
| WO | 0160994 | 8/2001 |

OTHER PUBLICATIONS

Berg et al., "Electric Field Effects on Bilogical Membranes:Electoincorporation and Electofusion",Ettore Maj Inter. Science, 1987,p. 135-166,vol. 32,Phys. Science, New York.

Kirson et al., "Disruption of Cancer Cell Replication by Alternating Electric Fields", Cancer Research 64, May 2004, p. 3288-3295, Haifa, Israel.

Asbury et al., "Trapping of DNA in Nonuniform Oscillating Electric Fields", Biophysical Journal, Feb. 1998, p. 1024-1030, vol. 74,Seattle, WA.

Janigro et al., "Alternating current electrical stimulation enhanced chemotherapy: a novel strategy to bypass multidrug resistance in tumor cells", BMC Cancer, 2006, 6:72.

Giladi et al., Microbial Growth Inhibition by Alternating Electric Fields, Antimicrobial Agents and Chemotherapy, Oct. 2008, p. 3517-3522.

Search Report and Written Opinion from corresponding application PCT/US2008/002134, Jan. 23, 2009.

\* cited by examiner

ELECTRODES FOR APPLYING AN ELECTRIC FIELD IN-VIVO OVER AN EXTENDED PERIOD OF TIME

CROSS-REFERENCE TO RELATED APPLICATIONS

This application is a divisional of application Ser. No. 11/294,780, filed Dec. 5, 2005, now U.S. Pat. No. 7,715,921, which claims the benefit of U.S. provisional application 60/633,871, filed Dec. 7, 2004. Each of those applications is incorporated herein by reference in its entirety.

BACKGROUND

This invention concerns electrodes for applying electric fields in-vivo over an extended period of time, and methods for using such electrodes.

Living organisms proliferate by cell division, including tissues, cell cultures, microorganisms (such as bacteria, mycoplasma, yeast, protozoa, and other single-celled organisms), fungi, algae, plant cells, etc. Dividing cells of organisms can be destroyed, or their proliferation controlled, by methods that are based on the sensitivity of the dividing cells of these organisms to certain chemical or physical agents. For example, certain antibiotics stop the multiplication process of bacteria.

It is well known that tumors, particularly malignant or cancerous tumors, grow very uncontrollably compared to normal tissue. Such expedited growth enables tumors to occupy an ever-increasing space and to damage or destroy tissue adjacent thereto. Furthermore, certain cancers are characterized by an ability to spread metastases to new locations where the metastatic cancer cells grow into additional tumors.

The rapid growth of tumors, in general, and malignant tumors in particular, as described above, is the result of relatively frequent cell division or multiplication of these cells compared to normal tissue cells. The distinguishably frequent cell division of cancer cells is the basis for the effectiveness of many existing cancer treatments, e.g., irradiation therapy and the use of various chemo-therapeutic agents. Such treatments are based on the fact that cells undergoing division are more sensitive to radiation and chemo-therapeutic agents than non-dividing cells. Because tumors cells divide much more frequently than normal cells, it is possible, to a certain extent, to selectively damage or destroy tumor cells by radiation therapy and/or chemotherapy. The actual sensitivity of cells to radiation, therapeutic agents, etc., is also dependent on specific characteristics of different types of normal or malignant cell types. Thus, unfortunately, the sensitivity of tumor cells is not sufficiently higher than that of many types of normal tissues. This diminishes the ability to distinguish between tumor cells and normal cells, and therefore, existing cancer treatments typically cause significant damage to normal tissues, thus limiting the therapeutic effectiveness of such treatments. Also, certain types of tumors are not sensitive at all to existing methods of treatment.

Electric fields and currents have been used for medical purposes for many years. The most common is the generation of electric currents in a human or animal body by application of an electric field by means of a pair of conductive electrodes between which a potential difference is maintained. These electric currents are used either to exert their specific effects, i.e., to stimulate excitable tissue, or to generate heat by flowing in the body since it acts as a resistor. Examples of the first type of application include the following: cardiac defibrillators, peripheral nerve and muscle stimulators, brain stimulators, etc. Currents are used for heating, for example, in devices for tumor ablation, ablation of malfunctioning cardiac or brain tissue, cauterization, relaxation of muscle rheumatic pain and other pain, etc.

Another use of electric fields for medical purposes involves the utilization of high frequency oscillating fields transmitted from a source that emits an electric wave, such as an RF wave or a microwave source, which is directed at the part of the body that is of interest (i.e., a target). In these instances, there is no electric energy conducting between the source and the body; but rather, the energy is transmitted to the body by radiation or induction. More specifically, the electric energy generated by the source reaches the vicinity of the body via a conductor and is transmitted from it through air or some other electric insulating material to the human body.

Electric fields that can be used in medical applications can thus be separated generally into two different modes. In the first mode, the electric fields are applied to the body or tissues by means of conducting electrodes. These electric fields can be separated into two types, namely (1) steady fields or fields that change at relatively slow rates, and alternating fields of low frequencies that induce corresponding electric currents in the body or tissues, and (2) high frequency alternating fields (above 1 MHz) applied to the body by means of the conducting electrodes or by means of insulated electrodes.

The first type of electric field is used, for example, to stimulate nerves and muscles, pace the heart, etc. In fact, such fields are used in nature to propagate signals in nerve and muscle fibers, central nervous system (CNS), heart, etc. The recording of such natural fields is the basis for the ECG, EEG, EMG, ERG, etc. The field strength in conductive electrode applications, assuming a medium of homogenous electric properties, is simply the voltage applied to the stimulating/recording electrodes divided by the distance between them. The currents thus generated can be calculated by Ohm's law and can have dangerous stimulatory effects on the heart and CNS and can result in potentially harmful ion concentration changes. Also, if the currents are strong enough, they can cause excessive heating in the tissues. This heating can be calculated by the power dissipated in the tissue (the product of the voltage and the current).

When such electric fields and currents are alternating, their stimulatory power, on nerve, muscle, etc., is an inverse function of the frequency. At frequencies above 1-10 kHz, the stimulation power of fields approaches zero. This limitation is due to the fact that excitation induced by electric stimulation is normally mediated by membrane potential changes, the rate of which is limited by the RC properties (with time constants on the order of 1 ms) of the membrane.

Regardless of the frequency, when such current inducing fields are applied, they are often associated with harmful side effects caused by currents. For example, one negative effect is the changes in ionic concentration in the various "compartments" within the system, and the harmful products of the electrolysis biological material, or the medium in which the tissues are imbedded.

Alternating fields of medium frequencies (about 50 kHz-1 MHz), which were traditionally assumed not to have any biological effect except due to heating, can be applied to a conductive medium, such as a human body, via insulated electrodes. Under such conditions the electrodes induce in the body only capacitive currents. In contrast to the general belief that such fields have no direct biological effect, in U.S. patent application Ser. Nos. 10/204,334, 10/288,562, 10/285,313 by Palti (each of which is incorporated herein by reference) and in a subsequent publication (Eilon D. Kirson, et al., Disruption of Cancer Cell Replication by Alternating Electric Fields, Cancer Res. 2004 64:3288-3295), such fields have been shown to have the capability to specifically affect cancer cells and serve, among others, for treating cancer.

Treatment of cancer, other diseases, conditions and pathophysiological states by alternating electric fields may require long term application (e.g., over weeks or months) of the fields to the target location, which involves correspondingly long contact between the electrodes and the body surface (e.g., the patient's skin). Such application may be associated with significant side effects that may result from both chemical and physical reactions. Such reactions have been reported upon application of TENS, muscle stimulation, long term body potential recording (EEG, ECG, etc.).

Chemical reaction may be due to the contact with the electrode itself, or the materials that are interposed between the electrode and the skin for improving electric conductivity (for example gel), and the products of the current flow including electrolysis at the electrode surfaces.

The long-term physical contact of the electrodes against the skin may effect the under-laying skin by the local pressure, by keeping the skin surface wet, or by the fact that the electrodes or gel, etc. occlude the exits of the skin appendages located at the external part of the skin, such as sweat glands, hair follicles, etc. This results in accumulation of water and chemical agents within the appendages and at the skin surface, which can damage the superficial skin layers.

SUMMARY OF THE INVENTION

The present invention is designed to eliminate, or significantly reduce some of the side effects associated with long term application of electric fields to the skin by using an electrode configuration that permits the skin to "breathe."

DETAILED DESCRIPTION OF PREFERRED EMBODIMENTS

Figure 1A:
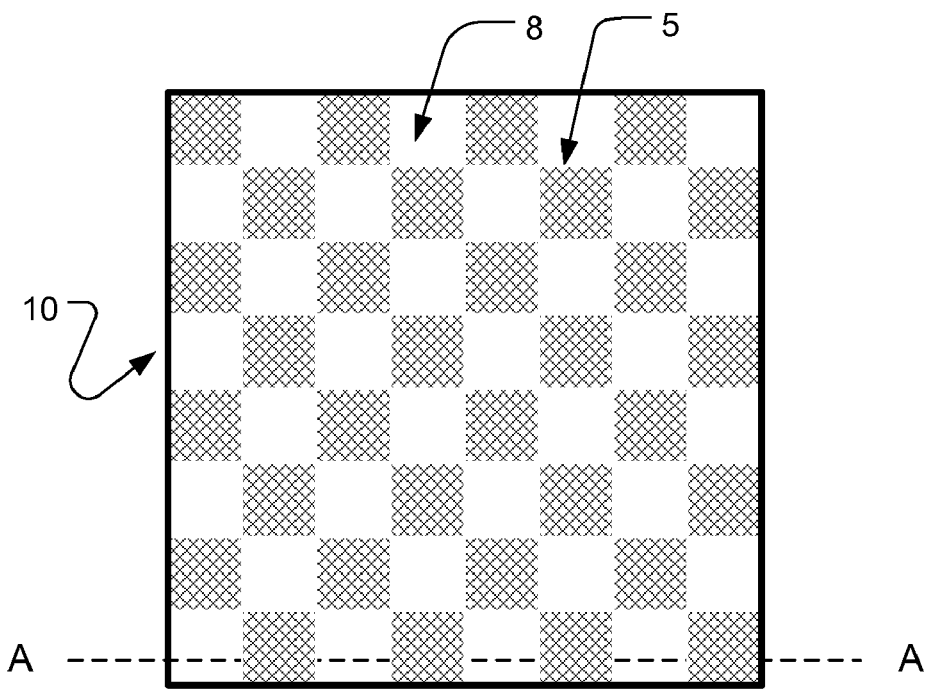
FIG. 1A is a plan view of a first embodiment of the present invention, which is a multi-segment electrode with the segments arranged in a rectangular array.
Figure 1B:
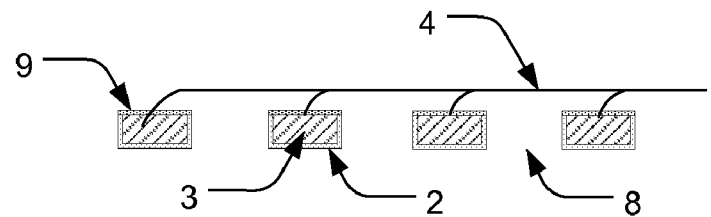
FIG. 1B is a cross section view of the FIG. 1A embodiment, taken along section line A-A.

FIGS. 1A and 1B depict a first embodiment of a composite electrode that is designed for applying an electric field to an in-vivo tumor for extended periods of time. The composite electrode 10 is made up of a number of individual segments 5, with a number of open spaces 8 disposed between the segments 5. The segments 5 apply an electric field to a desired location within the patient's body. Preferred characteristics of the applied field are described in the three patent applications identified above. Those applications teach that electric fields with frequencies between about 50 kHz to about 500 kHz (and more preferably between about 100 kHz and 300 kHz) at field strengths of between about 0.1 V/cm to about 10 V/cm (and more preferably between about 1 and about 10 V/cm) have proven effective at slowing or reversing the growth of rapidly dividing cells (e.g., cancer cells). For example, a 120 kHz, 1.4 V/cm field has been shown to be effective against melanoma, and a 170-250 kHz, 2.5 V/cm field has been shown to be effective against glioma.

Returning to FIGS. 1A and 1B, the segments 5 are preferably free to move about with respect to one another, to permit the electrode 10 to conform to the shape of the body's surface upon which the electrode 10 is placed. The segments 5 may be held together using any of a variety of suitable support structures, such as mounting them on a piece of cloth, netting, or other flexible backing (not shown). All of the segments are preferably electrically connected in parallel using appropriate wiring 4.

Each segment 5 preferably contains a conductive core 3 that is completely insulated from the surface upon which it is placed by a dielectric insulating material 2. Other surfaces of the segments 5 are preferably covered by any conventional insulating material 9. Because the dielectric insulating material 2 insulates the conductive core 3 from the surface of the patient's skin, any DC component that is present in the signal driving the electrodes will be blocked, and only the AC components at sufficiently high frequencies can pass into the patient's body. This configuration avoids the negative effects that would occur if conductive electrodes were used (e.g., ion concentration changes in the cells and the formation of harmful agents by electrolysis). This is because, in general, when capacitive electrodes are used, no actual transfer of charges takes place between the electrodes and the medium and there is no charge flow in the medium.

Figure 7A:
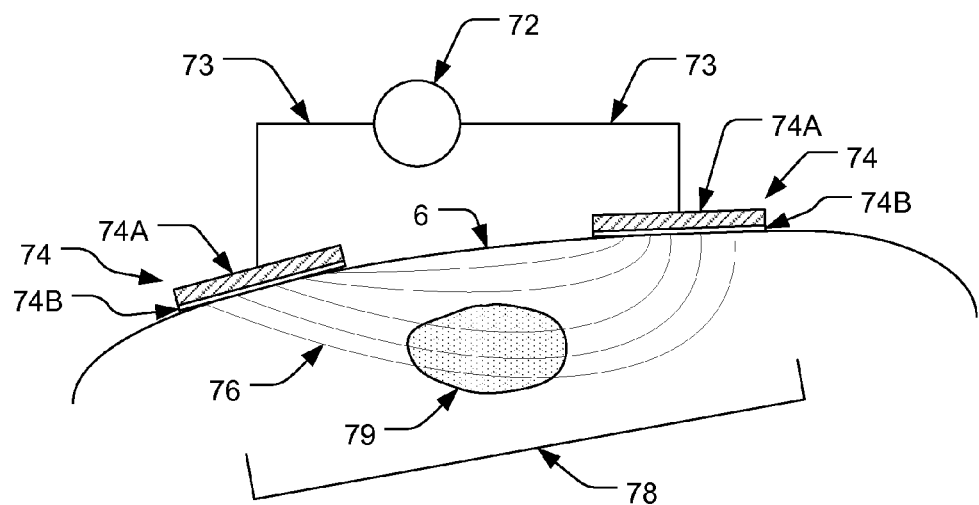
FIG. 7A is a pictorial representation showing how a pair of any of the aforementioned electrodes are placed in contact with the skin of a patient during use.
Figure 7B:
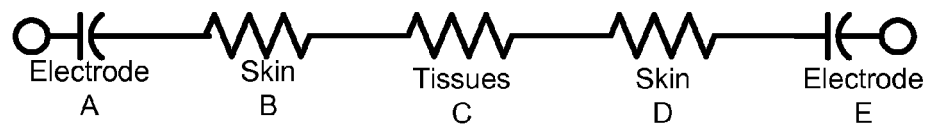
FIG. 7B is a schematic representation of an electrical circuit that is formed when a pair of any of the aforementioned electrodes are placed in contact with the skin of a patient.

FIG. 7A shows how the above-described electrodes (or the electrodes of the below-described embodiments) are used to apply the desired field to the target location. A pair of insulated electrodes 74 each contains a conducting portion 74A with an insulating dielectric portion 74B disposed thereon. When such electrodes are placed in contact with the patient's skin 6 and operatively connected to an AC voltage source 72 via leads 73, an electric field 76 is induced in the tissue 78 (which includes a tumor 79) that lies beneath the skin 6. As described in the three patent applications identified above, the equivalent electric circuit when the insulated electrodes are placed on the skin is as depicted in FIG. 7B: the dielectric coated electrodes 75 act as capacitors A, E, the skin 6 acts as a resistive load B, D, and the tissue 78 also acts as a resistive load C. Under these conditions, the relative values of the impedances cause the fraction of the potential difference (electric field) that falls on the electrode insulation to be strongly dependent on the capacitance of the electrodes A, E. The potential drop across the capacitive electrode A is A/(A+B+C+D+E), and a similar drop occurs across the other capacitive electrode E. At DC and low frequencies, the impedance of the capacitive electrodes A, E is high, and most of the voltage drop will be across the electrodes. In contrast, for extremely high frequencies, the capacitors have very low impedance and therefore a much larger portion of the voltage drop will appear in the tissue C. At the relevant frequency ranges identified above (i.e., from about 50 kHz to about 500 kHz), the impedance of the capacitive electrodes A, E will lie somewhere between those two extremes.

The preferred electric field intensity in the target tissue 79 is in the range of about 0.1 V/cm to about 10 V/cm. In order to achieve this voltage drop in the tissue C without increasing the voltage of the AC source 72 to undesirably high levels (which can pose a safety problem and be difficult to generate at the required parameters), the impedance of the capacitors A, E must be minimized, which occurs when the capacitance of the electrodes is maximized. Increasing the capacitance can be achieved by increasing the effective area of the "plates" of the capacitor, decreasing the thickness of the dielectric, or using a dielectric with a high dielectric constant. Since the electrode area is limited and the insulation thickness can not be reduced in view of potential dielectric breakdown and due to the danger of mechanical damage, the best way to deliver the appropriate fields to their target locations is to use dielectrics with a very high dielectric constant. Examples of suitable dielectrics are: KTN-Potassium Tantalate ($KTa_{1-x}Nb_xO_3$), or PMNT (Lead Magnesium Niobate Titanate), which all have dielectric constants above 1000. Note that with some of these high-K materials, the dielectric constant can vary dramatically depending on the material processing procedures that are used when the material is formed (e.g., crystallization or doping), and it is more preferable to use a variety with a dielectric constant above 10,000. Note, however, that a very thin coating by a strong dielectric material with a standard dielectric constant (e.g., 3-30) may also serve well under some configurations (e.g., if a weaker field or higher voltage is not problematic).

Returning now to FIGS. 1A and 1B, the electrodes 10 include spaces 8 that are distributed throughout the surface of the electrodes 10. These spaces 8 allow the skin beneath the electrode 10 to "breathe" by allowing air to reach the skin beneath the electrodes. As a result, moisture (e.g., sweat) that might otherwise build up on the surface of the skin can evaporate. This ameliorates the detrimental effects that can accompany long term use of non-perforated electrodes (as described above in the background section). In addition, the presence of the spaces 8 between the active segments 5 of the electrode 10 helps prevent heat (due to, e.g., dielectric losses and current flow) from building up beneath the electrodes 10.

To ensure that the field is effectively strong the target location, the spacing between the segments 5 of the electrodes 10 is preferably smaller than the distance from the surface to the location that is the target of the treatment (e.g., the tumor 79, shown in FIG. 7A). On the other hand, the spacing between the segments 5 is preferably larger than about 2 mm, and more preferably larger than about 4 mm, to provide adequate ventilation. In terms of area, the area of each space 8 is preferably larger than about 4 $mm^2$, and more preferably larger than about 16 $mm^2$. In this embodiment, the area of the segments 5 is roughly the same as the area of the spaces 8.

Figure 1C:
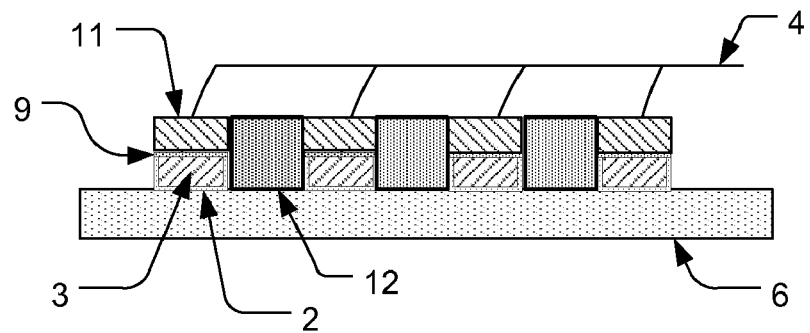
FIG. 1C is a cross section view of the FIG. 1A embodiment with an optional wicking feature added.
Figure 2:
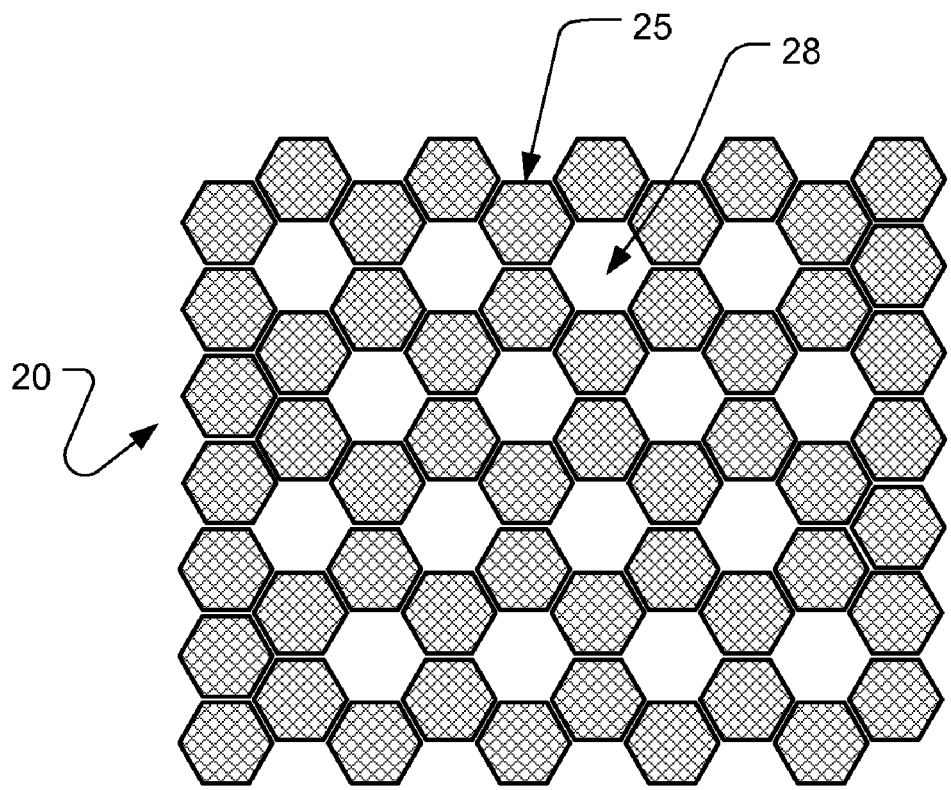
FIG. 2 is a plan view of a second embodiment of the present invention, which is a multi-segment electrode with the segments arranged in a hexagonal array.

FIG. 2 depicts a second embodiment of an electrode 20. This electrode 20 is very similar to the electrode 10 of the FIG. 1 embodiment, except that the segments 25 and the spaces 28 of the FIG. 2 embodiment are hexagonal instead of square. Of course, other shapes besides the depicted squares and hexagons may also be used, and the spacing between the segments may be varied as required. The spacing of the segments in these embodiments is preferably selected to provide an adequate amount of field at the target region, while providing adequate ventilation to the skin. The segmented structure of these embodiments can be particularly advantageous in anatomical positions where a large degree of flexibility is needed to conform the electrodes to the skin surface.

Figure 3:
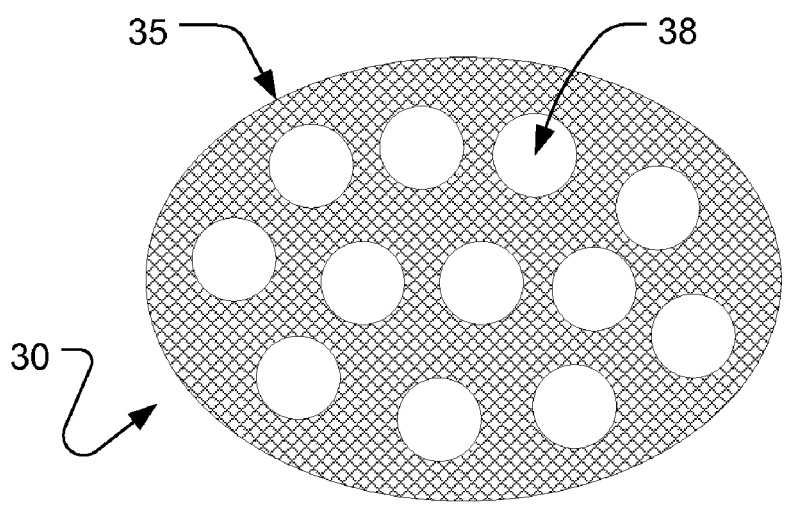
FIG. 3 is a plan view of a third embodiment of the present invention, which is a perforated electrode.

FIG. 3 depicts a third embodiment of an electrode 30. This electrode is preferably made of a single piece of conductive material 35, with perforations or holes 38 disposed therein. The lower surface of the electrode 30 (not shown), which contacts the skin of the patient, is preferably coated with a dielectric material similar to the dielectric 2 of the FIG. 1 embodiment. The upper surface of the electrode 30, which faces away from the patient during use, is preferably coated with an insulator similar to the insulator 9 of the FIG. 1 embodiment. The spacing of the holes in this embodiment is also preferably selected to provide an adequate amount of field at the target region, while providing adequate ventilation to the skin.

Figure 4A:
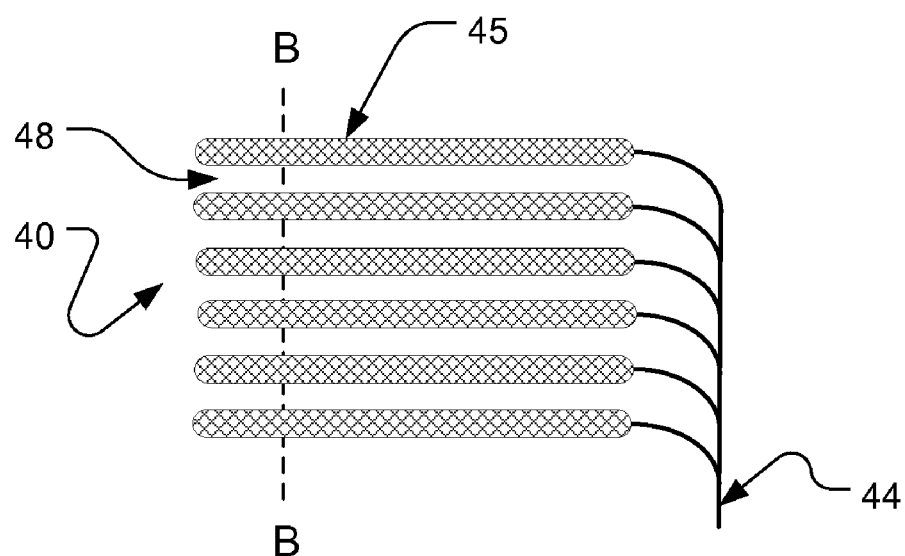
FIG. 4A is a plan view of a fourth embodiment of the present invention, which is an electrode made of a plurality of parallel wires.
Figure 4B:
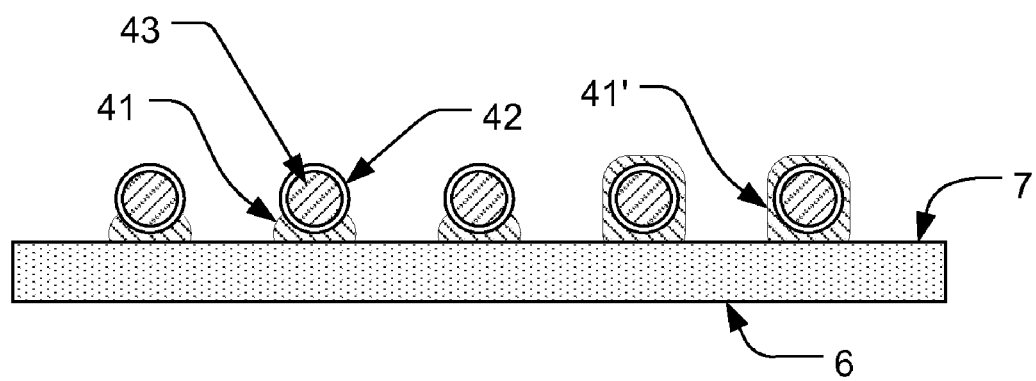
FIG. 4B is a cross section view of the FIG. 4A embodiment, taken along section line B-B used, used with a conductive gel.

FIGS. 4A and 4B are plan and section views of a fourth embodiment of an electrode 40. This electrode is made of a set of parallel elements 45 that are separated by spaces 48. Each element 45 is made of a conductive wire 43 that is surrounded by a dielectric coating 42, preferably of a material similar to the dielectric 2 of the FIG. 1 embodiment. The conductors 43 are preferably electrically connected in parallel by wires 44. A suitable backing (not shown) may be affixed to the electrode 40 to maintain the desired spacing of the elements 45 of the electrode 40. Optionally, this backing may be designed to prevent bending of the electrode along the length of the elements 45, which could crack the dielectric coating when a brittle dielectric is used. However, the backing may be configured to permit bending of the electrode 40 about an axis that is parallel to the elements 45, as long as the bending occurs at the spaces 48. The spacing of the open spaces 48 in this embodiment is also preferably selected to provide an adequate amount of field at the target region, while providing adequate ventilation to the skin. For example, the spaces 48 may be at least 2 mm wide, or more preferably, at least 4 mm wide.

Figure 5:
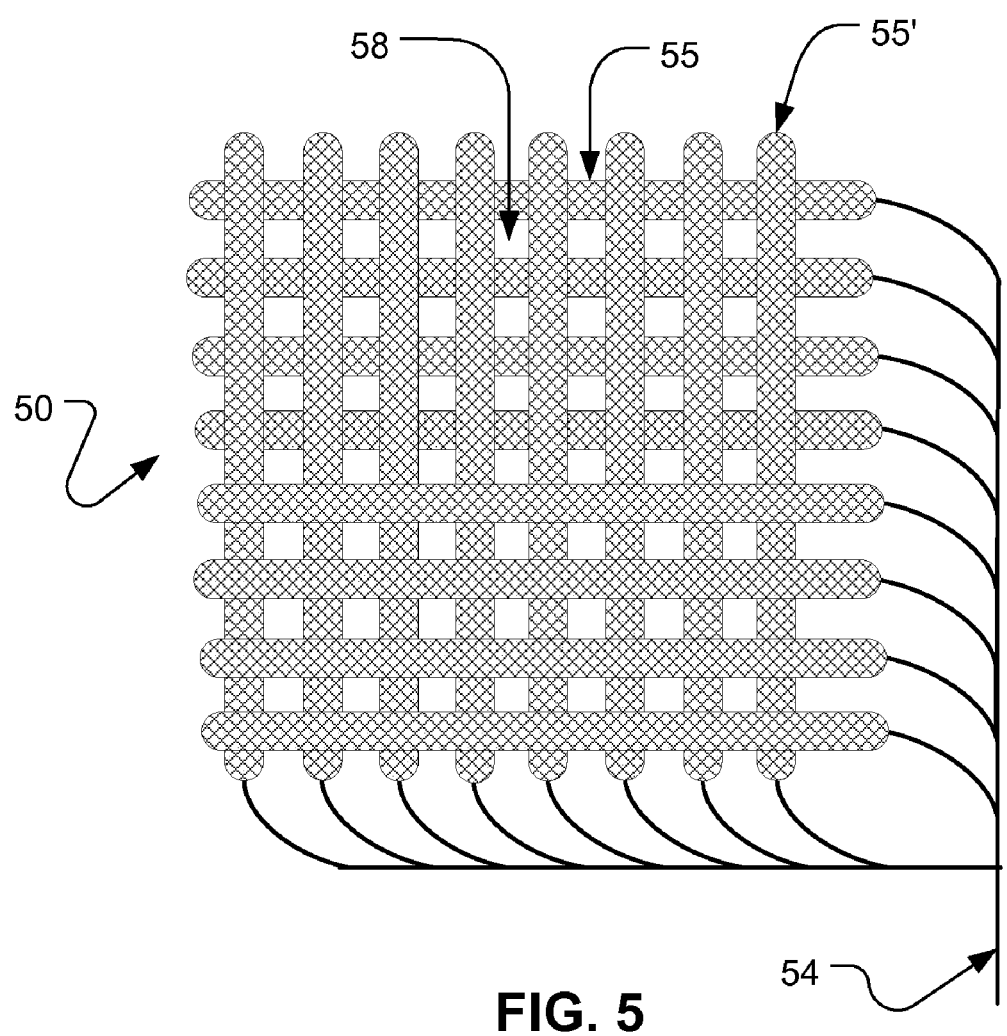
FIG. 5 is a plan view of a fifth embodiment of the present invention, which is an electrode made from a group of parallel wires, with an additional group of parallel wires that are perpendicular to the first group.

FIG. 5 is a plan view of a fifth embodiment of an electrode 50. This embodiment is similar to the FIG. 4 embodiment described above, except that in addition to the horizontal elements 55 that correspond to the horizontal elements 45 of the FIG. 4 embodiment, the fifth embodiment also contains a second set of vertical elements 55' with a similar construction. Both sets of elements 55, 55' are preferably wired up in parallel by wires 54. As with the above-describe embodiments, the size of the open spaces 58 are also preferably selected to provide an adequate amount of field at the target region, while providing adequate ventilation to the skin. For example, the spaces 58 may be at least 2 mm by 2 mm, or more preferably, at least 4 mm by 4 mm.

In some embodiments, e.g., FIGS. 1 and 4, the pattern of insulated conductors and spaces is configured so that locations that are covered when the electrode is positioned in a first location will become uncovered when the electrode is repositioned to a second location that is offset slightly from the first location, wherein the overall footprint of the electrodes in both locations is substantially the same. When this arrangement is implemented, the electrodes can be shifted back and forth between two positions periodically (e.g., every 2 to 4 days), so that each small patch of skin is alternately covered (in one position) or uncovered (in the other position).

Periodically exposing each patch of skin to the air in this manner gives the skin a chance to recover from any negative effects (e.g., accumulation of moisture or field effects) than may have occurred during the period of time when the skin was covered by the electrode. In applications where the electrodes are applied to the head, the head may be shaved before the electrodes are replaced in their new position, to prevent hair growth from interfering with the fields.

Figure 6A:
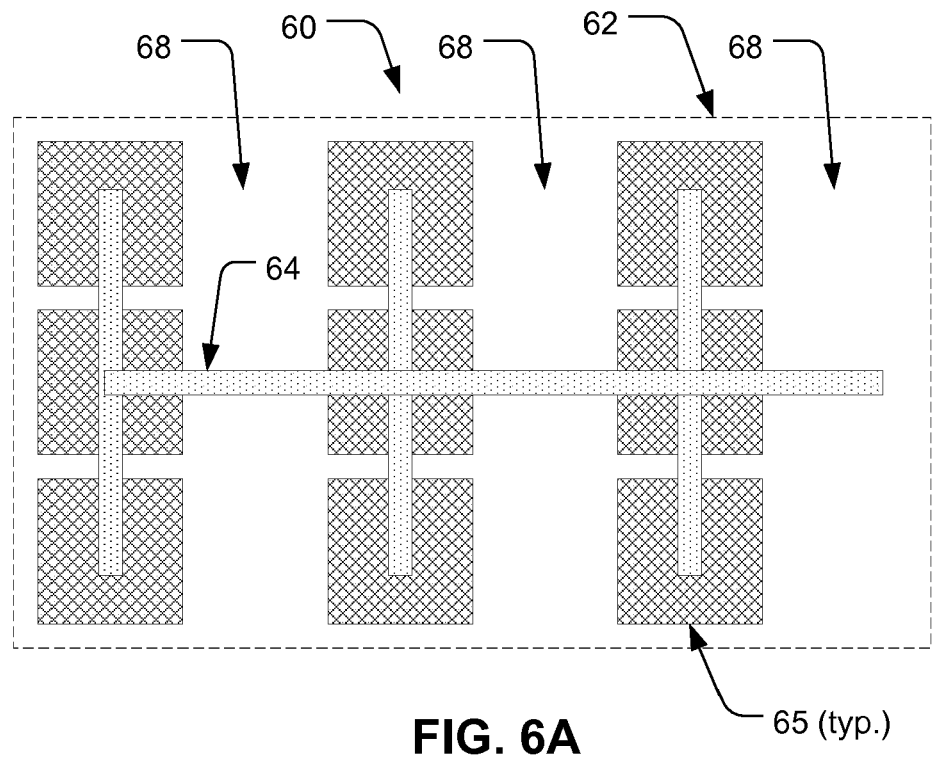
FIG. 6A is a plan view of a sixth embodiment of the present invention, with the electrode located at a first position within an overall footprint.
Figure 6B:
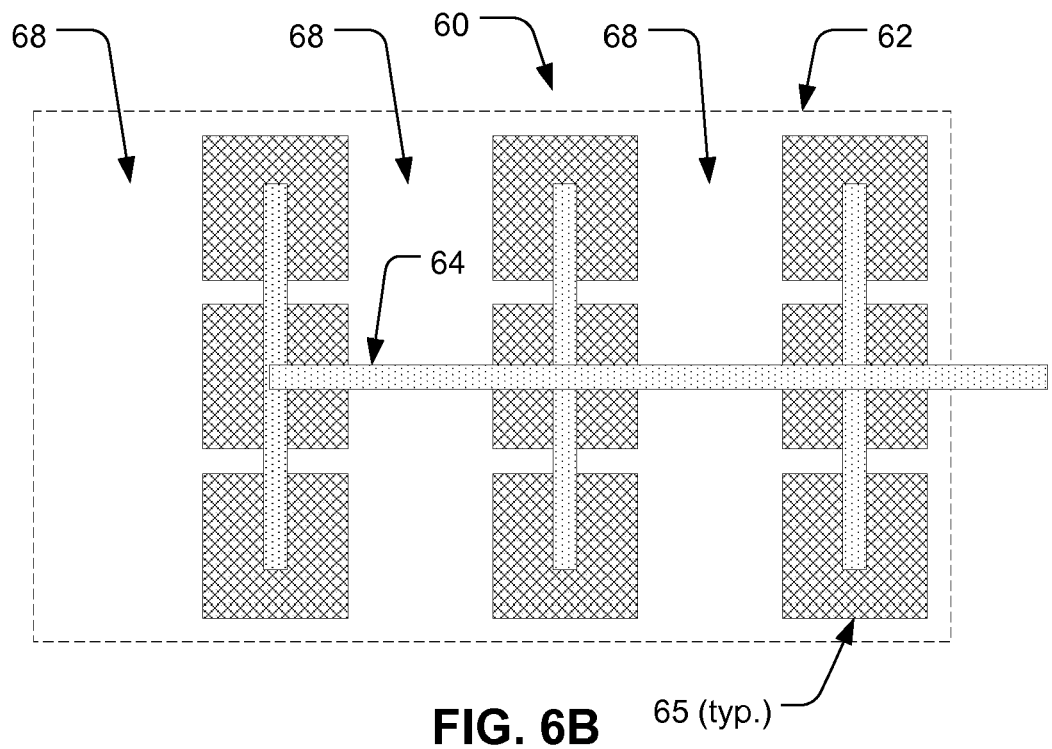
FIG. 6B shows the electrode of FIG. 6A located at a second position within an overall footprint.

FIGS. 6A and 6B are plan views of a sixth embodiment of an electrode 60 positioned, respectively, at first and second locations within an overall footprint 62. As such, FIGS. 6A and 6B depict yet another embodiment in which the electrodes can be shifted back and forth between two positions periodically, as discussed above. The electrode 60 of this embodiment is made of a set of square segments 65 that are separated by spaces 68, with the area of the segments 65 roughly the same as the area of the spaces 68. The construction of the individual segments 65 of this embodiment is preferably similar to the segments 5 described above in connection with the FIG. 1 embodiment. Each segment 65 preferably measures at least 2 mm by 2 mm, and more preferably at least 4 mm by 4 mm, with a thickness between about 0.2 and about 1 mm. Note that although square segments are depicted in FIGS. 6A and 6B, other shapes and sizes may also be used, such as rectangular segments (e.g., 5×15 mm or 13×15 mm), circular segments (e.g., 19 mm in diameter), or other shapes that are designed to conform to a particular anatomical location.

The segments 65 may be mechanically held in place by any suitable flexible support. For example, they may be mounted on a thin and flexible substrate such as DuPont Kapton® polyimide film (not shown). When such a film is used, flexible wiring 64 may also be integrated onto the substrate to provide a low impedance electrical connection between the segments 65. An adhesive bandage may be used to affix the electrode assembly to the patient's body, in which case the adhesive bandage would also provide additional mechanical support.

Optionally, temperature sensors (e.g., a thermistor, not shown) may be added to each segment in this embodiment, e.g., by mounting them through a small hole (e.g., 2.5 mm dia.) in the center of each segment. When a polyimide film with flexible wiring is used for the connections to the segments, the wiring for the sensors is preferably implemented on the same polyimide film.

FIG. 1C illustrates an optional additional skin protective system. In this case the spaces between the solid coated portions 3, 2 of the electrodes are filled with a water absorbing material 12 such as cotton, polypropylene, etc. that wicks the wetness off the skin 6 so as to keep it dry, and transfers it to a water storing medium 11 such as a hygroscopic gel, polyacrylate, etc. The water storing medium 11 is preferably positioned on the back of the electrode body so that it does not touch the skin. Note that while FIG. 1C illustrates this optional feature in connection with the FIG. 1A/1B embodiment, this feature may be incorporated into any of the other embodiments described above by making appropriate changes to the shapes and sizes of the water absorbing material 12 and the water storing medium 11.

FIG. 4B illustrates the use of another option—a conductive gel. (Note that while FIG. 4B is illustrates this optional feature in connection with the FIG. 4A embodiment, this feature may be incorporated into any of the other embodiments described above.) The electric contact between the cylindrical electrodes (which are made of conductors 43 surrounded by a dielectric coating 42) and the body surface 7 or skin can be improved by placing an intervening filler such as a conductive gel 41 between the electrodes and the skin 6. Alternatively, the gel 41' may be applied so as to completely surround the dielectric coating 42 that surrounds the conductor 43, which results in an increase in the area of the effective electrode surface. Optionally, the absorbing material 12 or gel 41' may include or be coated by a medication that prevents or relieves skin irritation and inflammation, such as a steroid paste.

Unfortunately, long term application of an object or medium that is not permeable to air, such as a gel, often results in skin reaction which may be severe. In addition water based media such as gels keep the skin wet, and long term wetting of the skin causes the external corneal skin layer to swell and lose its skin protective ability. Many gels can also occlude the orifices of the sweat and sebaceous glands, thus worsening the damage to the skin. Accordingly, such gels are preferably used in combination with those above-described embodiments where the electrodes can be shifted back and forth between two positions periodically, to minimize these problems.

Optionally a temperature sensor (not shown) may be incorporated into the electrode, and an appropriate circuit (not shown) can be used to temporarily turn off the power to the electrode (or to individual affected regions, if the segments are not all wired in parallel) when the output of the sensor indicates that it is too hot.

The above-described embodiments can generate safely and effectively alternating and transient electric fields in human patients, or other objects, for prolonged periods of time, by means of skin surface electrodes without causing significant side effects. Minor skin reactions that might still occur may be eased by incorporating medication to the conductive gels used. Such medication can include steroids, anti-allergic agents, antihistamines, etc.

While the invention has been particularly shown and described with reference to preferred embodiments thereof, it will be understood by those skilled in the art that various changes in form and details can be made without departing from the spirit and scope of the invention.

I claim:

1. A method of treating a patient with an AC electric field, comprising the steps of:
    placing at least two electrodes against a patient's body, the electrodes having a conductive substrate and a thin dielectric layer located between the patient and the conductive substrate, wherein at least one of the electrodes has a plurality of open spaces passing therethrough, the open spaces being distributed and sized to permit moisture that is located beneath the electrode to escape via the open spaces; and
    applying an AC voltage across the electrodes to induce an electric field at a target region in the patient's body, the electric field having a frequency between about 50 kHz and about 500 kHz and a field strength between about 0.1 and about 10 V/cm at the target region.

2. The method of claim 1, wherein the applying step lasts for at least five days.

3. The method of claim 1, wherein the electric field has a frequency between about 170 kHz and about 250 kHz and a field strength between about 1 and about 10 V/cm at the target region.

4. The method of claim 1, wherein the electric field has a frequency of about 120 kHz and a field strength between about 1 and about 10 V/cm at the target region.

5. The method of claim 1, wherein the conductive substrate is a single piece of conductive material.

6. The method of claim 1, wherein the conductive substrate comprises a plurality of separate sections that are attached to one another in a manner that permits the sections to move with respect to neighboring sections, by a limited amount.

7. The method of claim 1, wherein the conductive substrate comprises a plurality of roughly parallel wires spaced apart by at least 2 mm, and wherein the thin dielectric material surrounds each of the wires.

8. The method of claim 1, wherein the open spaces are at least 2 mm wide.

9. The method of claim 1, wherein the open spaces are at least 4 mm wide.

10. The method of claim 1, wherein the open spaces have an area that is least 4 square mm.

11. The method of claim 1, wherein the open spaces have an area that is least 16 square mm.

12. The method of claim 1, further comprising the step of moving the electrodes from a first position in which first portions of the surface of a patient's body are covered by solid portions of the electrodes to a second position in which the first portions are not covered by the solid portions of the electrodes, wherein the overall footprints of the electrodes in the first position substantially overlap the overall footprints of the electrodes in the second position.

13. The method of claim 12, wherein the electrodes are switched between the first position and the second position every 2-4 days.

14. A method of treating a patient with an AC electric field, comprising the steps of:
  placing at least two electrodes against a patient's body, the electrodes having a conductive substrate and a thin dielectric layer located between the patient and the conductive substrate, the dielectric layer having a dielectric constant of at least 1000, wherein at least one of the electrodes has a plurality of open spaces passing therethrough, the open spaces being distributed and sized to permit moisture that is located beneath the electrode to escape via the open spaces; and
  applying an AC voltage across the electrodes to induce an electric field at a target region in the patient's body, the electric field having a frequency between about 50 kHz and about 500 kHz and a field strength between about 0.1 and about 10 V/cm at the target region.

15. The method of claim 14, wherein the applying step lasts for at least five days.

16. The method of claim 14, wherein the electric field has a frequency between about 170 kHz and about 250 kHz and a field strength between about 1 and about 10 V/cm at the target region.

17. The method of claim 14, wherein the electric field has a frequency of about 120 kHz and a field strength between about 1 and about 10 V/cm at the target region.

18. The method of claim 14, wherein the conductive substrate is a single piece of conductive material.

19. The method of claim 14, wherein the conductive substrate comprises a plurality of separate sections that are attached to one another in a manner that permits the sections to move with respect to neighboring sections, by a limited amount.

20. The method of claim 14, wherein the conductive substrate comprises a plurality of roughly parallel wires spaced apart by at least 2 mm, and wherein the thin dielectric material surrounds each of the wires.

21. The method of claim 14, wherein the open spaces are at least 2 mm wide.

22. The method of claim 14, wherein the open spaces are at least 4 mm wide.

23. The method of claim 14, wherein the open spaces have an area that is least 4 square mm.

24. The method of claim 14, wherein the open spaces have an area that is least 16 square mm.

25. The method of claim 14, further comprising the step of moving the electrodes from a first position in which first portions of the surface of a patient's body are covered by solid portions of the electrodes to a second position in which the first portions are not covered by the solid portions of the electrodes, wherein the overall footprints of the electrodes in the first position substantially overlap the overall footprints of the electrodes in the second position.

26. The method of claim 25, wherein the electrodes are switched between the first position and the second position every 2-4 days.

27. The method of claim 14, wherein the dielectric layer has a dielectric constant of at least 10,000.

* * * * *